(12) United States Patent
Spreitzer et al.

(10) Patent No.: US 9,132,467 B2
(45) Date of Patent: Sep. 15, 2015

(54) METHOD AND TOOL FOR THE CYLINDRICAL DEFORMATION OF AN AL SLEEVE TO THE CORE DIMENSION OF THE INTERNAL PLASTIC CLOSURE, AS PREPARATION FOR A DIFFUSION-PROOF PRESS CONNECTION WITHIN THE TWO COMPONENTS

(75) Inventors: Joerg Spreitzer, Hahnheim (DE); Christoph Hahn, Sprendlingen (DE); Michael Huebner, Bacharach-Henschhausen (DE); Gerald Mathe, Waldalgesheim (DE); Peter Funke, Eichwalde (DE); Ruediger Pusch, Eichwalde (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1107 days.

(21) Appl. No.: 13/122,867

(22) PCT Filed: Oct. 8, 2009

(86) PCT No.: PCT/EP2009/063063
§ 371 (c)(1), (2), (4) Date: Jul. 19, 2011

(87) PCT Pub. No.: WO2010/040791
PCT Pub. Date: Apr. 15, 2010

(65) Prior Publication Data
US 2012/0090153 A1    Apr. 19, 2012

(30) Foreign Application Priority Data

Oct. 9, 2008    (EP) .................................... 08166264

(51) Int. Cl.
*B21D 39/04*    (2006.01)
*B21D 19/06*    (2006.01)
(Continued)

(52) U.S. Cl.
CPC .............. *B21D 39/048* (2013.01); *B21D 19/06* (2013.01); *B21D 51/2615* (2013.01); *B21D 51/54* (2013.01); *B23P 11/005* (2013.01); *A61M 15/009* (2013.01); *Y10T 29/49908* (2015.01)

(58) Field of Classification Search
CPC .. B21D 39/048; B21D 51/2615; B21D 51/54; B21D 19/06; B23P 11/005; Y10T 29/49908; A61M 15/009

USPC ........... 29/508, 510, 511, 422, 801, 243.517, 29/243.57, 515, 516, 267; 72/101, 110, 72/112, 120, 121, 122, 379.2, 379.4, 72/366.2, 452.5, 452.1, 216, 224; 413/1, 413/2, 4, 5
See application file for complete search history.

(56) References Cited

U.S. PATENT DOCUMENTS 3,067,709 A * 12/1962 Stankowski et al. ..... 29/243.517
3,236,081 A    2/1966 Kruse
(Continued)

FOREIGN PATENT DOCUMENTS

| CA | 2362243 A1 | 8/2000 |
| DE | 29500338 U1 | 3/1996 |

(Continued)

OTHER PUBLICATIONS

International Search Report, Form PCT/ISA/210, for corresponding PCT/EP2009/063063; date of mailing: Oct. 28, 2010.
(Continued)

*Primary Examiner* — Christopher M Koehler
(74) *Attorney, Agent, or Firm* — Michael P. Morris; Mary-Ellen M. Devlin

(57) ABSTRACT

In a method of producing a connection between the neck area of a light metal cartridge, particularly an aluminium cartridge, and a plastic container inserted therein, by a drawing process that forms a connection area and applies areas of the wall of the light metal cartridge against the plastic container using a rotating main body (15) of a drawing tool (2), said main body supporting at least one profiled drawing roller (3) which can rotate about a rotation axis (5) in order to delimit a tool working opening (1), wherein the drawing roller (3) lies against the outer surface of the light metal cartridge, the rotation axis (5) of the drawing roller (3) is arranged at a tool-internal end area of a lever (9) arranged transversely relative to the longitudinal axis (16) of the drawing tool (2), said lever being supported at its opposite tool-external end area on the drawing tool (2) so as to be pivotable about a pivot axis (11) in a force-controlled manner and so as to apply the drawing roller (3) against the outer surface of the light metal cartridge.

16 Claims, 3 Drawing Sheets

(51) Int. Cl.
  *B21D 51/26* (2006.01)
  *B21D 51/54* (2006.01)
  *B23P 11/00* (2006.01)
  *A61M 15/00* (2006.01)

(56) References Cited

U.S. PATENT DOCUMENTS

| | | | |
|---|---|---|---|
| 3,395,442 A * | 8/1968 | Herbenar | 29/441.1 |
| 3,473,359 A * | 10/1969 | Joslin | 72/121 |
| 3,662,450 A * | 5/1972 | Kish et al. | 29/237 |
| 4,578,982 A * | 4/1986 | Schrock | 72/402 |
| 4,771,625 A * | 9/1988 | Watanabe et al. | 72/121 |
| 5,411,521 A * | 5/1995 | Putnam et al. | 606/225 |
| 6,547,503 B1 | 4/2003 | Böhm | |
| 6,988,496 B1 | 1/2006 | Eicher et al. | |
| 7,802,568 B2 | 9/2010 | Eicher et al. | |
| 7,886,661 B1 * | 2/2011 | Goff et al. | 100/232 |
| 8,020,277 B2 * | 9/2011 | Melsheimer | 29/508 |
| 8,225,476 B2 * | 7/2012 | Mayfield | 29/283.5 |
| 8,474,122 B2 * | 7/2013 | Melsheimer | 29/508 |
| 2002/0138966 A1 * | 10/2002 | Motsenbocker | 29/516 |
| 2004/0011105 A1 * | 1/2004 | Nakamura et al. | 72/121 |
| 2004/0103716 A1 | 6/2004 | Klein | |
| 2007/0017089 A1 * | 1/2007 | Hosoi | 29/801 |

FOREIGN PATENT DOCUMENTS

| | | |
|---|---|---|
| DE | 19746018 A1 | 4/1999 |
| JP | S34-019729 | 12/1959 |
| JP | 62131743 U1 | 8/1987 |
| JP | 2002537192 A | 11/2002 |
| JP | 2003191014 A | 7/2003 |
| JP | 2005539241 A | 12/2005 |
| WO | 9621531 A1 | 7/1996 |
| WO | 0049988 A2 | 8/2000 |
| WO | 2006136427 A1 | 12/2006 |

OTHER PUBLICATIONS

Office Action for corresponding Japanese Application No. 2011-530485, dated Dec. 2, 2013.

* cited by examiner

METHOD AND TOOL FOR THE CYLINDRICAL DEFORMATION OF AN AL SLEEVE TO THE CORE DIMENSION OF THE INTERNAL PLASTIC CLOSURE, AS PREPARATION FOR A DIFFUSION-PROOF PRESS CONNECTION WITHIN THE TWO COMPONENTS

BACKGROUND

The invention relates to a method for producing a connection between the neck area of a light metal cartridge, particularly an aluminium cartridge, and a plastic container inserted therein, by a drawing process that forms a connection area and applies areas of the wall of the light metal cartridge against the plastic container using a rotating main body of a drawing tool, said main body supporting at least one profiled drawing roller which can rotate about a rotation axis in order to delimit a tool working opening, the drawing roller lying against the outer surface of the light metal cartridge.

The invention further relates to a drawing tool which comprises a rotating main body having at least one profiled drawing roller arranged on a circular track and rotatable about a rotation axis, wherein the drawing roller delimits a tool working opening and can be moved out of a position that defines a minimum tool working opening, enlarging the diameter of the tool working opening, counter to the force of a spring, into a position that defines a maximum tool working opening.

For administering inhalable pharmaceutical active substance formulations, inhalers are used that can be held in the patient's hand and operated manually, in which the pharmaceutical active substance formulation is contained in an inhaler cartridge which, once the active substance formulation has been used up, can be removed from the inhaler and replaced by a new inhaler cartridge. The inhaler cartridge consists of an external aluminium cartridge and a plastic container inserted therein, often a plastic container produced by coextrusion, which comprises a rigid outer container and a flexible inner bag disposed therein. In order to create a pressure equalising opening between the inner bag and the outer container, an opening is formed in the relatively rigid outer container, for example by the so-called cut/crack-open process. The plastic container is filled with the pharmaceutical active substance formulation and sealed and inserted in the aluminium cartridge in the course of the manufacturing process to form the inhaler cartridge. In a subsequent step, a deformed wall portion is then formed in the aluminium cartridge in the upper part of the thus assembled inhaler cartridge, this deformed wall portion lying against the outer surface of the plastic container inserted in the aluminium cartridge. To form the connection area at the upper edge of the aluminium cartridge a drawing process is used in which a rotating drawing tool travels with its tool working opening from above over the connection area of the aluminium cartridge that is to be formed and thereby brings profiled drawing rollers arranged around the tool working opening into contact with the outer surface of the aluminium cartridge, so as to form the connection area by an axial movement. Then, in subsequent finishing steps, the aluminium cartridge is pressed in gastight manner against the outside of the plastic container arranged therein. Then the combination of the aluminium cartridge with the plastic container inserted therein is subjected to further processing and machining steps, at the end of which the finished inhaler cartridge filled with pharmaceutical active substance formulation is obtained.

Various drawing tools are known in the art for carrying out the drawing process. Thus, there are drawing tools in which the profiled drawing rollers are configured to be displacement-controlled to form the profiled connection area. However, because of the manufacturing tolerances occurring in the manufacture of aluminium cartridges and plastic containers, lastingly satisfactory results cannot be achieved with drawing tools of this kind. Therefore, drawing tools have also been developed in which the drawing rollers are guided and moved by force control. With drawing tools of this kind, however, only about 20000 inhaler cartridges can currently be produced in long-term operation.

In a force-controlled drawing tool known from the art, a tilting lever actuated by spring force is mounted externally parallel to the longitudinal axis of the drawing tool so as to be pivotable about a pivot axis arranged perpendicularly to the longitudinal axis of the drawing tool. On the side remote from the spring, the tilting lever bears on a slide that carries a drawing roller. As a result of the spring force acing on the tilting lever, when the aluminium cartridge is inserted in the tool working opening this and every other drawing roller of the drawing tool constructed in the same way is pressed against the outer surface of the aluminium cartridge. As a result, when the aluminium cartridge is inserted into the tool working opening, the drawing rollers are able to give way outwardly initially counter to the force of the spring acting on the tilting lever.

In the manufacturing process with this drawing tool the stationary aluminium cartridge and the rotational drawing tool are initially guided synchronously over one another at the same speed so that the aluminium cartridge is positioned underneath the tool working opening of the drawing tool. Then the drawing tool is lowered onto the aluminium cartridge from above while still rotating, as a result of which the drawing rollers surrounding the tool working opening come into contact with the outer surface of the aluminium cartridge and are thereby also set in rotation. The drawing tool is then lowered further until the drawing rollers have completely gripped the outer surface that is to be deformed in order to form the connection area. This lowering action causes the profiled drawing rollers to perform the drawing process and thereby deform the wall of the aluminium cartridge in the connection area such that the inside of the wall of the aluminium cartridge lies against the outer surface of the plastic container inserted therein. In order to achieve a uniform wall thickness of the aluminium cartridge and prevent damage to the plastic container or aluminium cartridge, the drawing rollers can give way radially outwards, as described hereinbefore, in displacement-controlled manner, counter to the force of the compression spring acting on the tilting lever. The minimum tool working opening selected in the drawing tool is thus adjusted to a lower limit of about 0.2 mm, so that when an aluminium cartridge that is to be processed is inserted the drawing rollers are always operating under prestress. With this force-controlled tool, totally satisfactory results have not yet been achieved in practice, because of the absence of equalisation of tolerances.

In displacement-controlled drawing tools, the problem is that they are not reliably capable of equalising the tolerances of the individual components of an inhaler cartridge, such as the plastic inner container, the plastic closure of the plastic inner container, the aluminium cartridge and a silicon seal that is to be fitted. Consequently, when the tolerances fall short, for example, so-called chatter marks are produced on the neck of the deformation region formed on the aluminium cartridge. When the tolerances are excessive, e.g. if the closure of the plastic inner container is too big or if an aluminium cartridge is formed with too small a diameter, the material that is deformed and displaced during the drawing process is pressed upwards and extends the neck of the aluminium cartridge in an undesirable manner. In the subsequent machining step of the inhaler cartridge, namely flanging, unattractive edges or even so-called burrs are produced.

SUMMARY

The problem of the invention is to provide a method and a drawing tool of the kind mentioned hereinbefore which, on the one hand, make it possible to compensate deviations in dimensional tolerances and, on the other hand, ensure the tool service lives required for long-term operation.

In the method according to the invention the problem is solved in that the rotation axis of the drawing roller is arranged at a tool-internal end area of a lever arranged transversely relative to the longitudinal axis of the drawing tool, the lever being supported on the drawing tool at its opposite tool-external end area so as to be pivotable about a pivot axis in a force controlled manner and so as to apply the drawing roller against the outer surface of the light metal cartridge.

In the drawing tool the problem is solved according to the invention in that the rotation axis of the drawing roller is arranged at a tool-internal end area of a lever arranged transversely relative to the longitudinal axis of the drawing tool, the lever being supported on the drawing tool at its opposite tool-external end area so as to be pivotable about a pivot axis in a force controlled manner and so as to apply the drawing roller against the outer surface of the workpiece inserted in the tool working opening.

Advantageous and expedient further features and embodiments of the invention will become apparent from the respective sub-claims.

Both the method and the drawing tool are characterised by the formation of a lever acted upon by spring force and arranged at right angles to the drawing tool and at right angles to the longitudinal axis of the working area of the drawing tool that forms the tool working opening. At the tool-internal end of the lever the rotation axis of a rotatable drawing roller is associated with the lever, the rotation axis being movable about a pivot axis. At its tool-external end area the lever is mounted to be pivotable about a further pivot axis, while a force induced by the spring acts in this tool-external end area. As a result of this arrangement, on the one hand the drawing roller supported by the lever is able to swivel or move out of the way counter to the spring force, thereby enlarging the cross-section of the tool working opening and on the other hand the drawing roller is pressed and guided against the outer surface of the workpiece inserted in the tool working opening by the induced force in the way of an inward swivelling or travelling movement in order to perform a drawing process under force control. In this way, in one production step of the manufacture of an inhaler cartridge, it is possible, in a satisfactory manufacturing process, to press the upper end area of the aluminium cartridge against the outside of the plastic container already disposed in the aluminium cartridge, with deformation by drawing, and thereby form a connection in this area between the inside of the aluminium cartridge and the outside of the plastic container. The endurance times when using the drawing tool according to the invention are improved by the fact that the respective drawing roller, and advantageously all the drawing rollers, no longer perform a slide-controlled purely translatory movement in the radial direction of the tool working opening, but because they are arranged on the pivotable lever they perform a movement in the radial direction. As a result of this movement, the movement out of the range of the tool working opening and the movement into the range of the tool working opening are significantly gentler, both for the respective drawing roller and also for the workpiece that is to be machined. The lever arranged transversely of the longitudinal axis of the tool working opening and/or the drawing tool is preferably directed substantially perpendicularly to this longitudinal axis, i.e. substantially horizontally when the drawing tool is in operation.

In order to ensure force-controlled application of the respective drawing roller against the workpiece that is to be machined, a spring-induced force preferably acts on the tool-external end area of the lever and the connection area is formed by pivoting the lever, causing a pivoting movement that covers a pivot angle and a resultant force-controlled application of the drawing roller to the outer surface of the light metal cartridge, the drawing roller performing an axial movement thanks to another pivot axis.

As the method is preferably used to produce an inhaler cartridge for use in an inhaler for administration of active substance formulations by the patient himself, in one or more subsequent steps the plastic container is expediently connected in gastight manner to the light metal cartridge and filled with a pharmaceutical active substance formulation and sealed. Preferably, the light metal cartridge and the plastic container are then further processed to form an inhaler cartridge for use in an inhaler.

According to a feature of the drawing tool, a force induced by the spring acts on the tool-external end area of the lever and the lever can be pivoted about the pivot axis counter to this spring force such that the rotation axis can be moved out of the position of the drawing roller associated with the minimum tool working opening and back into this position.

In order to act on the lever and hence on the drawing roller arranged thereon under force control using only one spring, the tool-external region of the lever acts on an annular disc that is rotatably attached to the base at least in parts, on which the spring is mounted under pre-stress, while during the radial yielding movement of the drawing roller the tool-external region the annular disc is rotatable in parts counter to the force of the spring and the movement of insertion or inward motion of the drawing roller can be effected by a back-rotation of the annular disc, propelled by spring force, with force transmission introduced by the latter into the tool-external region of the lever. The annular disc confers particular advantages when a plurality of drawing rollers are arranged on one lever, as in this embodiment only one spring is required and in the event of one lever being jammed it is forcibly moved by means of the other levers associated with the annular disc. Moreover, the same force acts on all the drawing rollers.

In order to be able to eliminate radial play between the lever and the annular disc during the setting or adjustment of the drawing tool, the pivot axis in the tool-external region of the lever is formed in the centre of an eccentrically mounted sleeve that acts on the annular disc. The sleeve cooperates with the annular disc, in particular, with no play in the rotary direction of action of the drawing tool in order to manufacture a perfect workpiece in reproducible manner. Moreover the pivot axis serves as a pivotable mount for the corresponding pivot axis of the lever.

In order to produce a relatively linear yielding movement of the drawing roller for equalising tolerances, another pivot axis is formed in the region of the drawing roller.

In order to provide favourable lever ratios and achieve the movements needed to equalise the tolerances, expediently the two pivot axes are in the longitudinal axis of the lever and the centre point of the rotation axis is aligned laterally offset therefrom, the pivot axis in the region of the drawing roller being offset in particular by 1 mm relative to the rotation axis.

The distance between the additional pivot axis in the region of the drawing roller and the rotation axis forms a lever arm. Preferably, there is a lever ratio of 1:28 between the lever arm and the lever.

According to a further feature the additional pivot axis supports the drawing roller in eccentrically adjustable manner and is rotatably mounted in bearing flanges of a bearing block secured to the tool and is non-rotationally mounted on the lever. By moving the bearing block the drawing tool is adjusted, in order to fix the size of the tool working opening and hence the external diameter of the connection area between the cylindrical aluminium cartridge and the plastic container inserted therein.

Expediently, the radial movement of the drawing roller when giving way allows a roller travel of 0.3 mm and the lever then covers a pivot angle of 22°.

In order to obtain a precise shaping of the machined area of the wall, particularly in the case of circular cylindrical light metal cartridges, there are preferably at least three drawing rollers, preferably five drawing rollers, arranged on the main body, which surround the tool working opening at an equal spacing from one another.

It will be understood that the features mentioned above and still to be described hereinafter may be used not only in the particular combination stated but also in other combinations. The scope of the invention is defined only by the claims.

BRIEF DESCRIPTION OF THE DRAWING

The invention is hereinafter described in more detail by means of an embodiment by way of example with reference to the associated drawings, wherein.

DETAILED DESCRIPTION

Figure 1:
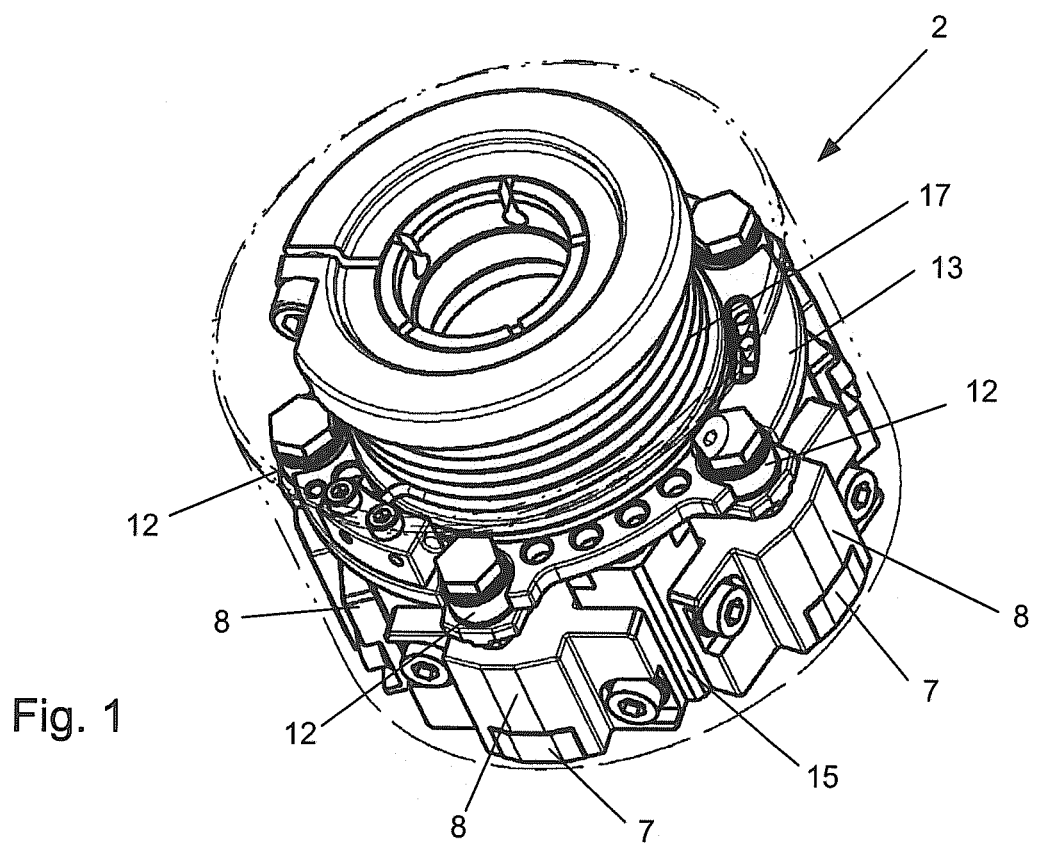
FIG. 1 shows a perspective view of the drawing tool.
Figure 2:
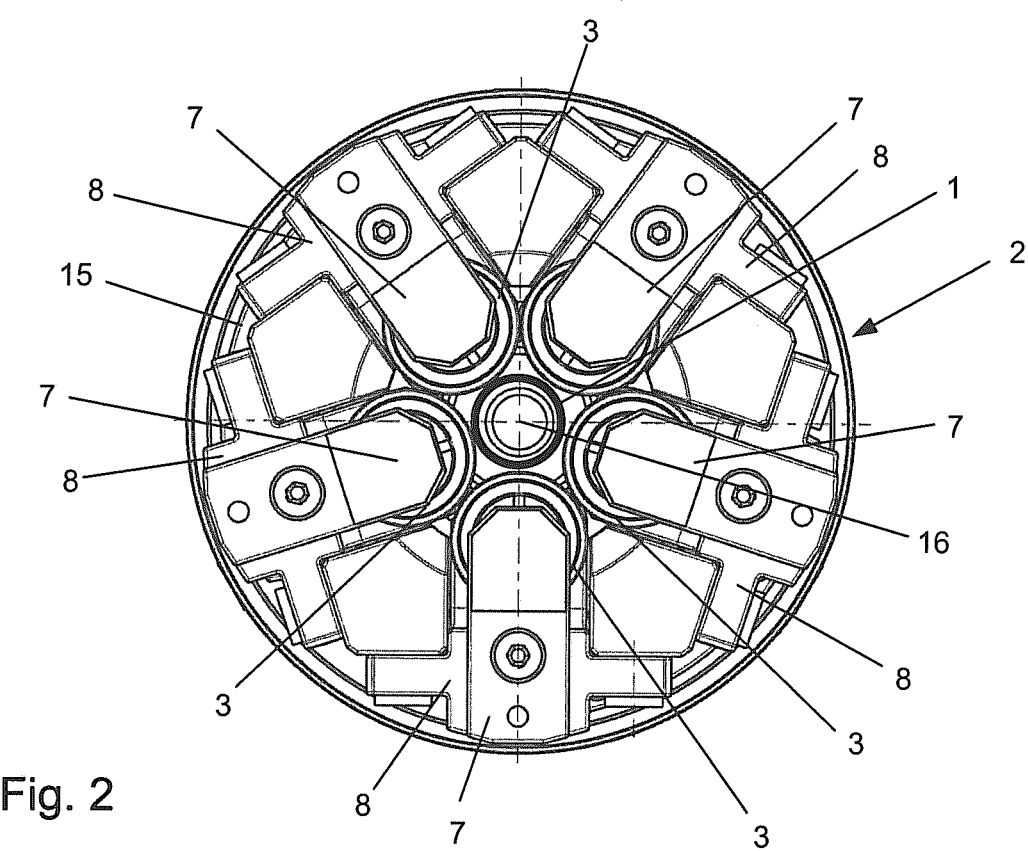
FIG. 2 is a view of the drawing tool according to FIG. 1 from below.
Figure 3:
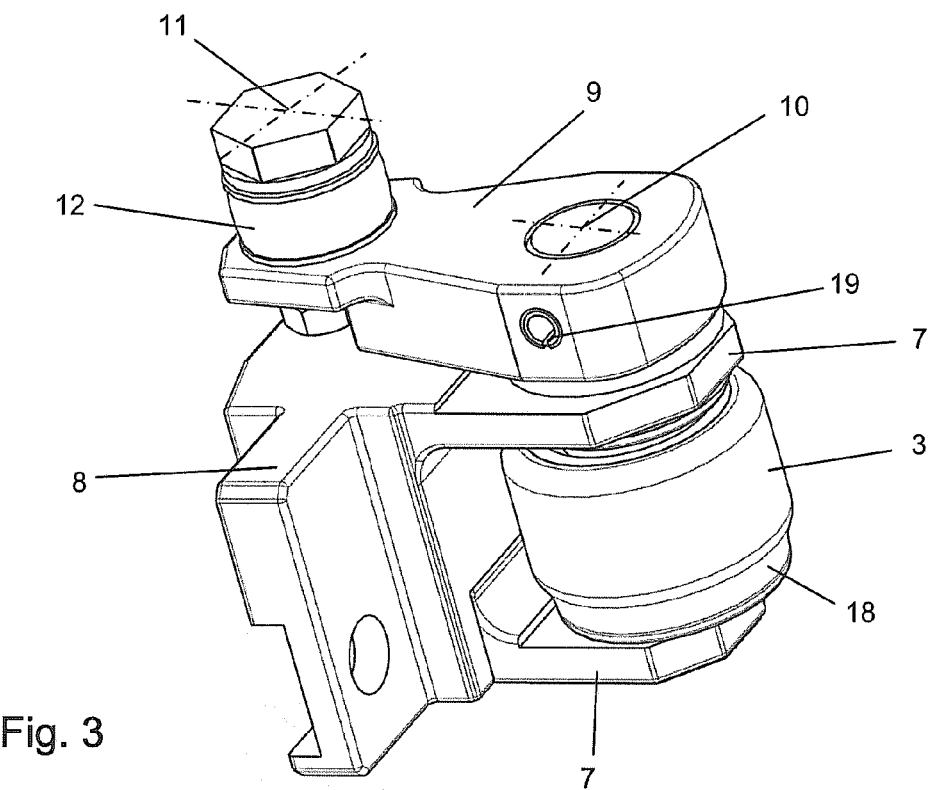
FIG. 3 shows a perspective view of a roller unit of the drawing tool
Figure 4:
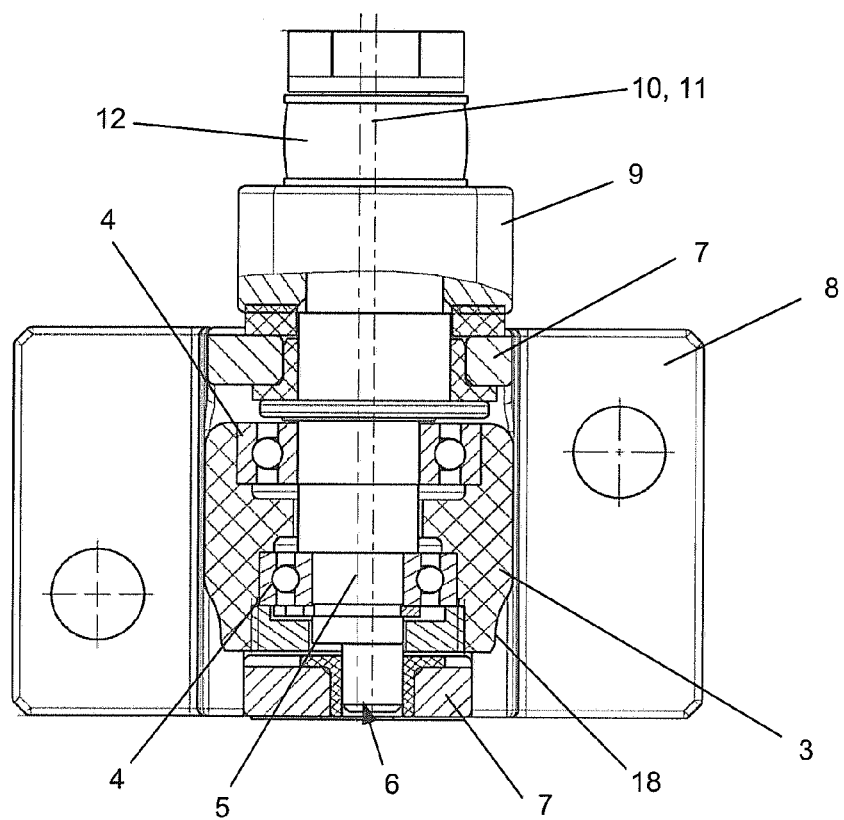
FIG. 4 is a cross-section through the roller unit according to FIG. 3.
Figure 5:
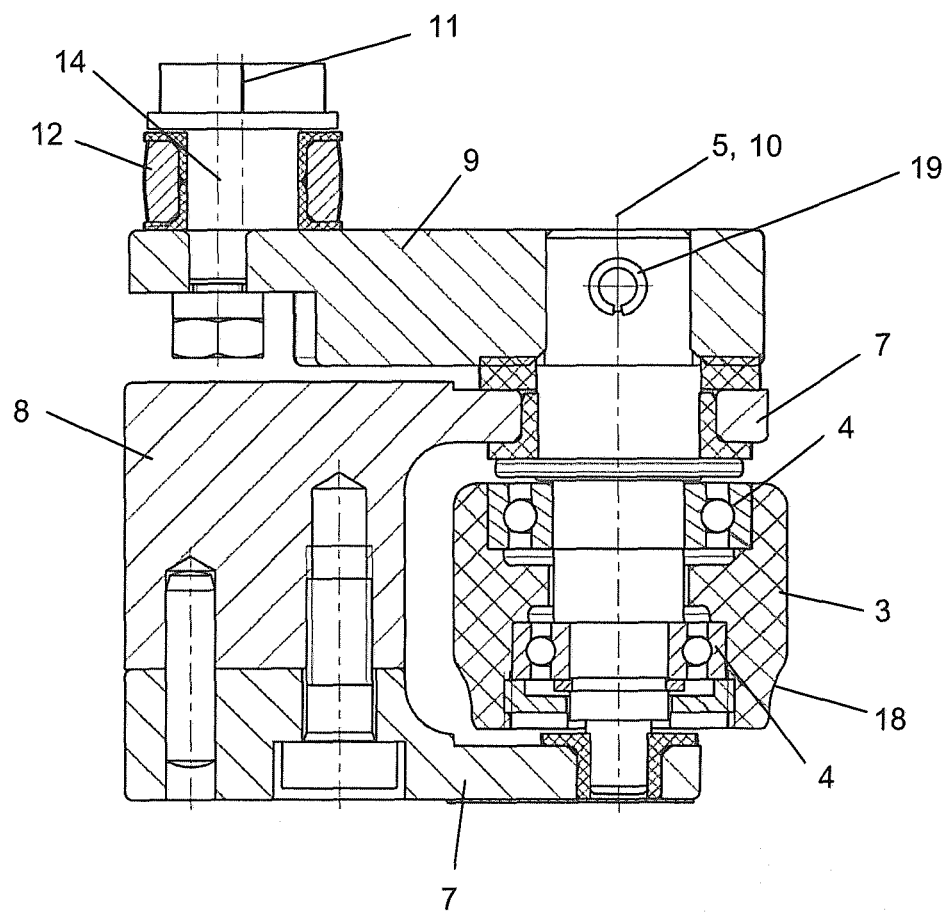
FIG. 5 is a longitudinal section through the roller unit according to FIG. 3.

For carrying out a drawing process, a tool working opening 1 is formed in the centre of a rotatable drawing tool 2 on the inside thereof, the opening being formed by five drawing rollers 3 running on a circular path surrounding the tool working opening 1. Only one of the drawing rollers 3 is described hereinafter, as all the drawing rollers 3 are of identical construction.

The drawing roller 3 is rotatably secured by means of two ball bearings 4 on an eccentric spindle 6 forming a rotation axis 5, the eccentric spindle 6 being eccentrically rotatable in two bearing flanges 7 of a bearing block 8 of the drawing tool 2 that accommodate the drawing roller 3 between them. One end of the eccentric spindle 6 protruding beyond the bearing block 8 is mounted non-rotationally by means of a transverse pin 19 on a tool-internal end area of a lever 9. The central axis of the eccentric spindle 6 offset laterally from the rotation axis 5 forms a pivot axis 10. At its tool-external end area opposite the drawing roller 3 the lever is held on an annular disc 13 so as to be pivotable about a further pivot axis 11 by means of a sleeve 12 surrounding said axis 11. The two pivot axes 10, 11 coincide in their normal position and the sleeve 12 is movably mounted on the lever 9 by means of an eccentric 14.

The annular disc 13 is mounted on a main body 15 of the drawing tool 2 so as to be rotatable about the longitudinal axis 16 thereof counter to the force of a spring 17 in the form of an annular spring. One end of the spring 17 engages in the annular disc 13 and the other end of the spring 17 is secured to the main body 15 of the drawing tool 2. The lever 9 is aligned transversely with respect to the longitudinal axis 16 of the drawing tool 1.

In order to adjust the drawing tool 2, the tool working opening 1 is adjusted by means of a plug gauge to a diameter which the desired external diameter of a light metal cartridge. The bearing blocks 8 are displaced and the rotation axes 5 of the drawing rollers 3 are aligned in a laterally offset position. By rotating the eccentric 14, the sleeves 12 are made to lodge in corresponding recesses in the annular disc 13, the recesses accommodating the sleeves 12 with some play.

In the operational state, the drawing tool 2 rotates and a workpiece, i.e. the light metal cartridge with a plastic container disposed therein, is introduced into the tool working opening 1. The drawing tool 2 travels axially downwards onto the workpiece and the approach gradients 18 of the drawing rollers 3 move into engagement with the workpiece, whereupon the drawing rollers rotate about their rotation axes. During a further downwardly directed axial movement, the workpiece is tapered by the drawing rollers 3 and a shoulder is shaped by the approach gradients 18.

To ensure that the workpiece is not damaged but still obtain a satisfactory connection between the neck area of the light metal cartridge and the plastic container inserted therein, each lever 9 performs a pivoting movement counter to the force of the spring 17, leading to substantially radial movements of the drawing rollers 3 to enlarge the diameter of the tool working opening 1. The corresponding deflection movements take place along the pivot axes 10, 11 of the lever 9 in the region of the rotated annular disc 13 and the rotating drawing roller 3. The drawing rollers 3 remain in the machining position, under spring bias, until the drawing tool 2 is moved out of engagement with the workpiece in an axial movement. Then the drawing rollers 3 take up their adjusted position, as a result of the action of the spring 17. At the same time the annular disc 13 is rotated by the force of the spring 17 and the levers 9 are pivoted so as to shift the drawing rollers 3.

In the embodiment, five drawing rollers 3 are shown. However, the drawing tool 2 may also have any other desired number of drawing rollers 3, particularly one or three drawing rollers 3.

The lever 8 extending between the sleeve 10 abutting on the annular disc 11 and the pivot axis 10 associated with the drawing roller 3 is in a ratio of 1:28 to the lever arm that is formed between the rotation axis 5 of the drawing roller 3 and the associated pivot axis 10.

The centre point of the pivot axis 10 and the centre point of the rotation axis 5 are arranged on the lever 9, laterally offset from one another, while preferably the centre point of the rotation axis 5 is arranged, in particular, 1 mm outside the longitudinal axis of the lever 9 and the centre point of the pivot axis 10 is arranged on the longitudinal axis of the lever 9. The outward pivoting movement of the lever 9 allows a degree of travel of the drawing rollers 3 of 0.3 mm in each case and in so doing covers a pivot angle of 22°.

The invention claimed is:

1. A method of producing a connection between the neck area of a light metal cartridge and a plastic container inserted therein, by a drawing process, the method comprising:
   providing a rotating main body (15) of a drawing tool (2), said main body rotating about a centrally located longitudinal axis (16), the main body supporting at least three profiled drawing rollers (3) which are each rotatable about respective rotation axes (5) in order to delimit a tool working opening (1), where each of the rotation axes (5) are parallel to, and radially spaced away from, the longitudinal axis (16) of the main body, inserting the light metal cartridge, with the plastic container disposed therein, into the tool working opening (1), pressing the drawing rollers (3) toward the centrally located longitudinal axis (16) such that each of the rotation axes (5) are biased radially toward, and remain parallel to, the longitudinal axis (16) of the main body, and such that the drawing rollers (3) are pressed against an outer surface of the light metal cartridge, wherein each of the rotation axes (5) of the respective drawing rollers (3) is arranged at a respective tool-internal end area of a respective lever (9), wherein each lever (9) extends transversely relative to the longitudinal axis (16) of the drawing tool (2), and wherein each lever (9) is supported on the drawing tool (2) at a respective opposing tool-external end area so that each lever (9) is pivotable about a pivot axis (11) in a force-controlled manner and so that each of the drawing rollers (3) is pressed against the outer surface of the light metal cartridge, and rotating the main body (15) about the centrally located longitudinal axis (16), while the drawing rollers (3) are engaged against the outer surface of the light metal cartridge, such that each of the respective rotation axes (5) rotate about, and remain parallel to, the centrally located longitudinal axis (16) while each drawing roller (3) rotates about its rotation axis (5), thereby forming a connection area and applying areas of a wall of the light metal cartridge against the plastic container using the drawing tool (2).

2. The method according to claim 1, further comprising providing a force on the tool-external end area of each lever (9) to pivot each lever (9), thereby producing a respective pivoting movement covering a respective pivot angle, and a resultant force-controlled application of each drawing roller (3) against the outer surface of the light metal cartridge.

3. The method according to claim 1, wherein the plastic container is connected in gastight manner to the light metal cartridge in one or more subsequent steps and is filled with a pharmaceutical active substance formulation and sealed, and/or the light metal cartridge and the plastic container are then further processed to form an inhaler cartridge for use in an inhaler.

4. The method according to claim 1 wherein the drawing tool (2) comprises a rotatable main body (15) having at least one profiled drawing roller (3) arranged on a circular track and rotatable about a rotation axis (5), wherein the drawing roller (3) delimits a tool working opening (1) and can be moved out of a position that defines a minimum tool working opening (1), enlarging the diameter of the tool working opening (1), counter to the force of a spring (17), into a position that defines a maximum tool working opening, characterised in that the rotation axis (5) of the drawing roller (3) is arranged on a tool-internal end area of a lever (9) aligned transversely with respect to the longitudinal axis (16) of the drawing tool (2), said lever (9) being supported at its opposite tool-external end area on the drawing tool (2) so as to be pivotable about a pivot axis (11) in a force controlled manner and so as to apply the drawing roller (3) against the outer surface of the workpiece introduced into the tool working opening (1).

5. The method according to claim 1, wherein the light metal cartridge is an aluminium cartridge.

6. A drawing tool which comprises:
a main body (15) that is rotatable about a centrally located longitudinal axis (16);
at least three profiled drawing rollers (3) coupled to the main body and located at uniform angular spacings from one another around the longitudinal axis (16), each drawing roller (3) being rotatable about a respective rotation axis (5), where each of the rotation axes (5) are parallel to, and radially spaced away from, the longitudinal axis (16) of the main body;
a mounting mechanism configured to orient each of the drawing rollers (3) such that: (i) each rotation axis (5) remains substantially parallel to the longitudinal axis (16) of the main body (15), and (ii) the drawing rollers (3) are radially slidable toward, and away from, the longitudinal axis (16), thereby defining a tool working opening (1) between the drawing rollers (3) that is movable between a minimum tool working opening and a maximum tool working opening;
at least three levers (9), each lever (9) being elongate in a longitudinal dimension aligned transversely with respect to the longitudinal axis (16) of the main body (15) of the drawing tool (2), an inner end of each lever (9) being coupled to a respective one of the drawing rollers (3), and an opposite outer end of each lever (9) being supported so as to be pivotable about a respective pivot axis (11) and thereby move the drawing rollers (3) between the minimum tool working opening and the maximum tool working opening; and
one spring (17) applying a biasing force to the at least three levers (9) that urges the drawing rollers (3) toward the minimum tool working opening in a force controlled manner and so as to urge the drawing rollers (3) against the outer surface of a workpiece introduced into the tool working opening (1).

7. The drawing tool according to claim 6, wherein the biasing force induced by the spring (17) acts on the outer end of each lever (9), such that each lever (9) is pivotable about the respective pivot axis (11) and the drawing rollers (3) moveable between the minimum tool working opening and the maximum tool working opening.

8. The drawing tool according to claim 6, further comprising:
an annular disc (13) attached to the main body (15) and rotatable about the longitudinal axis (16), wherein:
the outer end of each lever (9) is coupled to the annular disc (13) such that the inner end of each lever (9) rotates about the respective pivot axis (11) in response to rotation of the annular disc (13) about the longitudinal axis (16);
the spring (17) applies the biasing force to the levers (9) by way of applying a rotational force to the annular disc (13); and
the annular disc (13) being rotatable in parts counter to the rotational force of the spring (17) and insertion movement of each drawing roller (3) being achievable by a back-rotation of the annular disc (13) via the rotational force.

9. The drawing tool according to claim 6, wherein the respective pivot axis (11) of each lever (9) is formed in the outer end thereof and through a centre of an eccentrically mounted sleeve (12) which engages the annular disc (13).

10. The drawing tool according to claim 6, wherein a respective further pivot axis (10) is formed in a region of each of the at least three drawing rollers (3).

11. The drawing tool according to claim 10, wherein the respective pivot axis (11) and respective further pivot axis (10) of each lever (9) and the rotation axis (5) of a respective one of the drawing rollers (3) are aligned laterally offset from one another.

12. The drawing tool according to claim 11, wherein a respective distance between the respective further pivot axis (10) in the region of a respective one of the drawing rollers (3) and the respective rotation axis (5) thereof forms a respective lever arm.

13. The drawing tool according to claim 12, wherein each lever arm has a lever ratio of 1:28 between such lever arm and a respective one of the at least three levers (9).

14. The drawing tool according to claim 11, wherein each further pivot axis (10) supports the respective drawing roller (3) in an eccentrically movable manner and the respective drawing roller (3) is rotatably mounted by respective bearing flanges (7) of a bearing block that is attached to the drawing tool and is mounted in a rotation-locked manner on the respective lever (9).

15. The drawing tool according to claim 6, wherein each of the drawing rollers (3) is movable by 0.3 mm in response to a pivot angle of 22° of each lever (9).

16. The drawing tool according to claim 6, wherein the at least three drawing rollers (3) include five drawing rollers (3), arranged on the main body (12), at a uniform spacing from one another, delimiting the tool working opening (1).

* * * * *